United States Patent [19]

Bernstein

[11] 4,181,726

[45] Jan. 1, 1980

[54] METHOD OF ALLEVIATING PRURITIS

[76] Inventor: Joel E. Bernstein, 615 Brierhill Rd., Deerfield, Ill. 60015

[21] Appl. No.: 961,239

[22] Filed: Nov. 16, 1978

[51] Int. Cl.² .......................................... A61K 31/485
[52] U.S. Cl. .................................................... 424/260
[58] Field of Search ........................................ 424/260

[56] References Cited

U.S. PATENT DOCUMENTS 3,254,088   5/1966   Lewenstein et al. ............ 424/260 X

*Primary Examiner*—Leonard Schenkman
*Attorney, Agent, or Firm*—Vogel, Dithmar, Stotland, Stratman & Levy

[57] ABSTRACT

An improved method of relieving severe itching associated with conditions such as Hodgkin's Disease, mycosis fungoides, intractable pruritis and the like comprising administering an effective dosage of naloxone to a patient suffering from such itching.

4 Claims, No Drawings

METHOD OF ALLEVIATING PRURITIS

BACKGROUND OF THE INVENTION

Itching or pruritis is a common dermatologic symptom. The causes of pruritis are complex and poorly understood. The best understood mechanism of itching is the release of histamine in the skin leading to urticarial wheals and intense itching. Such itching has traditionally been relieved by antihistamines. While antihistamine therapy is often effective, the sedation and drowsiness produced by antihistaminic agents limits their effectiveness.

Many kinds of itching are not however easily relieved by antihistamines. For example, conditions such as Hodgkin's Disease, mycosis fungoides and severe jaundice produce intense itching unrelieved by antihistamines. Therefore, there is a need for improved treatment to relieve severe itching which can be not only an alternative to antihistaminic treatment of itching which responds to such treatment, but which further provides relief in intractable cases of pruritis which heretofore have been virtually impossible to treat. The present invention provides such a method.

Naloxone is a narcotic antagonist which is not known to cause physical or psychological dependence and which exhibits essentially no pharmacological activity in non-addicts. Naloxone is normally given by injection to addicts to assist them in narcotic withdrawal and sometimes is administered to post operative patients for partial reversal of narcotic depression following the use of narcotics during surgery.

It has been found surprisingly that naloxone is useful in alleviating severe itching in various conditions.

SUMMARY

The present invention provides an improved method of treating severe itching comprising administering a therapeutically effective amount of naloxone or a pharmaceutically acceptable salt thereof to a mammalian patient in need of such treatment.

DETAILED DESCRIPTION OF PREFERRED EMBODIMENTS

Naloxone hydrochloride is commercially available from Endo Laboratories, Inc., a subsidiary of the DuPont Company, 1000 Stewart Avenue, Garden City, New York 11530. The preparation of naloxone is disclosed in U.S. Pat. No. 3,254,088.

In the practice of this invention, naloxone is administered to patients suffering from severe itching in dosages of from 0.4 to 1000 milligrams, 2–8 times a day. It has been found that subcutaneous administration to patients having intractable pruritis have an onset of action of 5 to 10 minutes with a duration of action of from 2 to 3 hours. Oral administration of naloxone to patients with severe itching provides a delayed onset of action of about 20 minutes, but a more prolonged duration of action of roughly 5 hours. The following examples further illustrate the present invention.

EXAMPLE 1

0.4 milligrams of naloxone hydrocholoride, obtained from the Endo Pharmaceutical Company, was administered to a 120 pound, 49 year old black patient suffering from intractable pruritis secondary to biliary cirrhosis. This patient received 2 injections of 0.4 mg. of naloxone, 3 hours apart. The injections relieved the itching with an onset of action of 5 minutes and a duration of action of 120–180 minutes.

EXAMPLE 2

0.4 milligrams of naloxone hydrochloride, obtained from the Endo Pharmaceutical Company, was administered to a 150 pound, 55 year old white patient suffering from intractable pruritis secondary to uremia. The patient received 2 injections of 0.8 mg of naxolone, 3 hours apart. The injections relieved the itching with an onset of action of 5 minutes and a duration of action of 180 minutes.

EXAMPLE 3

400 milligrams of naloxone hydrochloride, obtained from the Endo Pharmaceutical Company, was administered subcutaneously to a 25 year old black patient weighing 180 pounds and suffering from a giant urticartia. The injection relieved itching 8 minutes and relief was obtained for 150 minutes.

EXAMPLE 4

1 gram of naloxone, obtained from the Endo Pharmaceutical Co., was administered orally to a 70 year old white patient weighing 125 pounds suffering from severe itching. Relief from itching was obtained after 20 minutes and relief from a single oral dose of 1 gram was provided for 300 minutes.

While naloxone is generally administered parenterally when used as a narcotic antagonist and is generally available commercially in parenteral dosage forms, it may be more desirable to treat the symptoms of pruritis by oral routes of administration, and the present invention also provides oral compositions suitable for treating the symptoms of pruritis.

This the present invention includes within the scope thereof, pharmaceutical compositions suitable for oral administration comprising, as the active ingredient thereof, naloxone or a pharmaceutically acceptable salt thereof and a pharmaceutically acceptable carrier or diluent.

Solid dosage forms for oral administration include capsules, tablets, pills, powders, and granules. In such solid dosage forms, the active compound is admixed with at least one inert diluent such as sucrose, lactose or starch. Such dosage forms can also comprise, as is normal practice, additional substances other than inert diluents, e.g. lubricating agents such as magnesium stearate. In the case of capsules, granules tablets and pills, the dosage forms may also comprise buffering agents. Tablets and pills can additionally be prepared with enteric coatings, if desired.

Liquid dosage forms for oral administration include pharmaceutically acceptable emulsions, solutions, suspensions, syrups and elixirs containing inert diluents commonly used in the art, such as water. Besides such inert diluents, compositions can also include adjuvants such as wetting agents, emulsifying agents and suspending agents and sweetening, flavoring and performing agents.

The following example further illustrates the present invention to exemplifying a pharmaceutical composition suitable for oral administration.

EXAMPLE 5

Tablets weighing one gram and having the following composition are formulated:

| Ingredient | Mg. |
| --- | --- |
| Naloxone Hydrochloride | 500 |
| Starch | 450 |
| Colloidal Silica | 47 |
| Magnesium Stearate | 3 |

The term pharmaceutically acceptable salts, as used herein, refers to the physiologically acceptable acid addition salts of naloxone such as the hydrochloride, hydrobromide, hydroiodide, acetate, valerate, oleate, etc.

It will be apparent to those skilled in the art that only the preferred embodiments have been described by way of exemplification and that there are various modifications which fall within the scope of this invention.

I claim:

1. A method of relieving severe itching in mammalian patients in need of such treatment, said method comprising administering a therapeutically effective amount of naloxone or a pharmaceutically acceptable salt thereof to a patient in need of such treatment.

2. The method of claim 1 comprising administering naloxone or a salt thereof by a parenteral route of administration.

3. The method of claim 1 wherein said naloxone or a salt thereof is administered by the oral route of administration.

4. The method of claim 1 wherein naloxone or a pharmaceutically acceptable salt thereof is administered to a patient in need of such treatment in dosages of from 0.4 to 1000 mg., 2–8 times a day.